(12) United States Patent
Stark et al.

(10) Patent No.: US 7,816,332 B2
(45) Date of Patent: Oct. 19, 2010

(54) STABLE AQUEOUS SOLUTION OF NATAMYCIN FUNGICIDE

(75) Inventors: Jacobus Stark, Rotterdam (NL); Ferdinand Theodorus Jozef Van Rijn, Delft (NL)

(73) Assignee: DSM IP Assets B.V., Te Heerlen (NL)

( * ) Notice: Subject to any disclaimer, the term of this patent is extended or adjusted under 35 U.S.C. 154(b) by 289 days.

(21) Appl. No.: 10/558,701

(22) PCT Filed: Jun. 1, 2004

(86) PCT No.: PCT/EP2004/005970

§ 371 (c)(1), (2), (4) Date: Nov. 30, 2005

(87) PCT Pub. No.: WO2004/105491

PCT Pub. Date: Dec. 9, 2004

(65) Prior Publication Data

US 2006/0241061 A1    Oct. 26, 2006

(30) Foreign Application Priority Data

Jun. 2, 2003  (EP) .................... 03076700

(51) Int. Cl.
*A01N 43/04* (2006.01)
*A01N 25/00* (2006.01)

(52) U.S. Cl. .................. 514/31; 514/836; 514/970; 424/405

(58) Field of Classification Search ............ 514/31
See application file for complete search history.

(56) References Cited

U.S. PATENT DOCUMENTS

| 3,343,968 | A |   | 9/1967 | Huhtanen |
| 3,378,441 | A |   | 4/1968 | Bridger |
| 4,148,891 | A | * | 4/1979 | Smink ................. 514/31 |
| 4,826,822 | A |   | 5/1989 | Anderson et al. |
| 5,686,273 | A |   | 11/1997 | Eisenschink et al. |
| 5,821,233 | A | * | 10/1998 | Van Rijn et al. ............ 514/31 |
| 6,146,675 | A | * | 11/2000 | Cirigliano et al. ........ 426/330.6 |
| 6,150,143 | A |   | 11/2000 | Raghoenath et al. |

FOREIGN PATENT DOCUMENTS

| GB | 1 470 005 | 4/1977 |
| WO | WO 92/10580 | 6/1992 |
| WO | WO 95/07998 | 3/1995 |
| WO | WO 95/08918 | 4/1995 |
| WO | WO 95/27073 | 10/1995 |
| WO | WO 97/29207 | 8/1997 |
| WO | WO 2006/045831 A1 | 5/2006 |

OTHER PUBLICATIONS

Harry Brik, "Natamycin"; Analytical Profile of Drug Substances; vol. 10, 1981, pp. 513-561.
Database Biosis, Biosciences Information Service, 1978, XP-002254989.
International Search Report.
Written Opinion and International Search Report mailed Feb. 16, 2006 in PCT/EP2005/055592.

* cited by examiner

*Primary Examiner*—Johann R Richter
*Assistant Examiner*—Nathan W Schlientz
(74) *Attorney, Agent, or Firm*—Nixon & Vanderhye P.C.

(57) ABSTRACT

The present invention provides an aqueous composition comprising—water; —a water miscible solvent; —and a polyene fungicide which is dissolved in the water and water miscible solvent. The present invention further provides a method for the production of the composition of the invention. The composition of the invention may be used as an antifungal treatment for a variety of products including food, feed, agricultural products, growth substrates and in- or outsides of buildings.

16 Claims, No Drawings

US 7,816,332 B2

STABLE AQUEOUS SOLUTION OF NATAMYCIN FUNGICIDE

This application is the US national phase of international application PCT/EP2004/005970 filed 1 Jun. 2004 which designated the U.S. and claims benefit of EP 03076700.8, dated 2 Jun. 2003, the entire content of which is hereby incorporated by reference.

BACKGROUND OF THE INVENTION

The present invention relates to the preparation of a stable aqueous solution which comprises a polyene fungicide and the use of such a solution to treat food, feed, agricultural products, growth substrates of crops and other materials on which fungi, including moulds or yeasts, can grow. This solution can also be used for pharmaceutical or cosmetic purposes. Products, substrates and materials treated with the solution of the invention are also disclosed.

The prevention of fungal growth is an important topic throughout the world. Many food, feed, agricultural products or other natural products can be considered as good substrates for fungal growth. Also crops can easily suffer from fungal infection, especially when grown at high humidity or in poor weather conditions. It is also well known that the growth substrate of many crops can be a source of fungal contamination. Finally, fungi can also grow inside and outside buildings on e.g. building materials, equipment, walls and all kind of wooden materials. This can in some cases lead to severe fungal problems in houses and factories.

Apart from serious economic losses, fungal growth is also a severe health risk. Growth of fungi may lead to introduction of fungal mycotoxins into the food chain. Fungal growth in houses not only looks ugly, but also introduces fungal particles into the air which might lead to allergic reactions and breathing problems.

Polyene fungicides can be used to prevent fungal growth in a wide variety of applications. An example of a polyene fungicide is natamycin. For more than 30 years, natamycin has been used to prevent fungal growth on food products.

Treatment with natamycin is extremely effective in preventing fungal growth on solid products, which require protection for a longer period of time. Cheeses and sausages are well known examples of food products, where surface treatments with natamycin is used very successfully.

A natamycin suspension can be added to the polymer dispersion that is applied to the cheese rind as a coating. Whole cheeses, shredded cheese or sausages can also be treated with a suspension of natamycin in water by spraying. Finally cheeses and sausages can also be dipped in a natamycin suspension.

Such treatments are not only efficient but also very convenient for food products, which are ripened or stored in the open air. After the treatment the surface of the product, the surface contains a mixture of dissolved and solid natamycin. Only the dissolved fraction has antifungal activity, whereas the more stable crystals ensure a prolonged working time.

The level of dissolved natamycin continuously decreases due to its interaction with fungi, diffusion or physical and chemical degradation. However, the level of active dissolved natamycin is maintained for a long period of time due to the slow release of natamycin from the crystals and diffusion over the surface of the product. Under these practical conditions, the sensitivity of fungi is far below the solubility of natamycin and, as a result, this is a very effective method of preventing fungal growth. Under normal hygienic conditions, several applications of these kind of treatments have proven to be effective.

Natamycin has a minimal inhibitory concentration of less than 5 ppm for most yeasts and of less than 10 ppm for most foodborne fungi. The solubility of natamycin in water at neutral pH levels is 30 ppm (Brik, H.; "Natamycin" Analytical Profiles of Drug Substances 10, 513-561 (1981)). Therefore for many applications, a treatment with a natamycin suspension is quite effective: the level of dissolved active natamycin is high enough to prevent the outgrowth of fungi while the undissolved fraction forms a depot.

However, for many other applications, a prolonged working time is less (or not at all) required. For such applications, the undissolved inactive fraction can be considered as redundant. Moreover, during preparation, stable aqueous natamycin suspensions have hardly any antifungal activity available just after adding the natamycin powder to the water. Even in cases where stirring devices are used, it takes several hours before the maximum amount of 30 ppm natamycin is dissolved. In cases of high contamination levels, unhygienic conditions or less sensitive fungal species, even higher amounts of active natamycin than the actual solubility in water are desired. In all these cases, there is a need for a stable and ready-to-use formulation in which the optimal amount of active fungicide is available quickly.

The solubility of polyene fungicides can be improved using alkaline or acidic conditions. However, the fungicide dissolves rapidly and is also rapidly decomposed under such conditions. Therefore, in practice, such preparations will not be used.

Modified crystal structures of polyene fungicides, solvates such as methanol solvates and calcium or barium salts as described in European Patent Application No. 670676 as improving the release of the compound from the crystals resulting in an improved activity. These compounds have in general a higher potential of dissolving the polyene fungicide. However, the dissolved fraction will be transformed to the thermodynamically most stable solid form when suspended in an aqueous environment. The fast release is only temporary and will not actually enhance the solubility of the polyene fungicide.

It can be concluded that there is a need for a stable natamycin solution which a concentration above the maximum solubility in water wherein the natamycin can be dissolved rapidly. However, up to now, it has not been possible to prepare such stable solutions. Even the quick preparation of stable solutions within the known physical limitations was not possible.

SUMMARY OF THE INVENTION

The invention provides an aqueous composition comprising:
    water;
    a water miscible solvent; and
    a polyene fungicide which is dissolved in the water and water miscible solvent.

The invention also provides a method for the production of an antifungal compostion which comprises mixing together:
    water;
    a water miscible solvent; and
    a polyene fungicide,
wherein the polyene fungicide is present in an amount such that the polyene fungicide dissolves in the water and the water miscible solvent.

The invention further provides the use of a composition of the invention as an antimicrobial agent.

DESCRIPTION OF THE INVENTION

The present invention provides a method for the preparation of an aqueous composition comprising a solution of polyene fungicide, and a water miscible solvent. Preferably the aqueous composition is a stable aqueous composition. The composition can contain an increased or desired amount of dissolved fungicide. The composition is preferably a solution. The composition produced by the method of the invention is also part of the present invention. By stable aqueous composition is meant an aqueous composition comprising polyene fungicide, preferably natamycin, which after 9 days of storage at 6° C. in a dark room comprises at least 50%, preferably at least 70%, more preferably at least 80%, even more preferably at least 90% or most preferably at least 95% of the initial amount of polyene fungicide. Preferably this activity is tested at a concentration of 200 ppm of the polyene fungicide. A percentage of the initial amount of polyene fungicide is measured by comparing the activity of natamycin with a fresh sample of natamycin.

The stable aqueous composition of the present invention is prepared by mixing together water, a water miscible solvent and the polyene fungicide, which is preferably natamycin. The polyene fungicide preferably dissolves within 5 minutes, even when 200 ppm solutions are made. Therefore, the stable aqueous composition of the invention is preferably a solution comprising water, a water miscible solvent and dissolved polyene fungicide. The water miscible solvent content of the composition is preferably from 0.1 to 10% (w/w). The polyene fungicide concentration is preferably from 5 to 1000 ppm.

Advantageously the stable aqueous composition can be prepared by the following method:
(a) preparing an alkaline or acidic aqueous liquid (e.g. a solution) containing a solvent and adjusting the pH, for example, using well known methods;
(b) preparing a concentrated solution of a polyene fungicide by adding the polyene fungicide to the alkaline or acidic aqueous solution; and
(c) diluting the concentrated solution with an aqueous liquid preferably containing a pH neutralizing agent or more preferably a buffer.

Surprisingly stable solutions of polyene fungicides can be prepared rapidly using this method. Advantageously, the polyene fungicide can be dissolved very quickly using the process of the invention. More surprisingly, the polyene fungicide is stable and has a markedly enhanced solubility in compositions with a relative very low amount of solvent and a pH between 5 and 8.

The aqueous liquid used in the method of the invention is preferably water. The pH of the aqueous system to which the polyene fungicide will be added is preferably from 1 to 4 or from 10 to 14. The pH is preferably above 10. The pH can be adjusted using well known methods by adding suitable acidic or alkaline compounds.

Examples of suitable acidic compounds are HCl, $H_2SO_4$, citric acid and lactic acid. Examples of suitable alkaline compounds are NaOH, KOH and $NH_4OH$.

The ratio solvent to water in the alkaline or acidic aqueous liquid depends on the type of solvent and the pH of the aqueous liquid. Any suitable ratio can be used. However the ratio of solvent to water is from 10:90 to 90:10, or more preferably from 30:70 to 70:30.

Any suitable solvent or mixture of solvents can be used. Suitable solvents systems are water miscible solvents. It will be appreciated that water miscible solvent together with water should be capable to keep the dissolved polyene fungicide in dissolved state at a pH between 5 and 8. Water miscible solvents include lower alcohols such as methanol, ethanol, propanol, butanol, methoxy-ethanol, ethylene glycol, propylene glycol and glycerol. Other examples of suitable solvents are, methyl formate, ethyl formate, formamide, acetone, dichloromethane, 1,2-dichloroethane, acetonitrile, dimethylformamide, dimethyl sulphoxide and N,N-dimethyl formamide. In situations where the composition of the present invention is to be applied to agricultural products or food or feed products, a food grade solvent such as ethanol is preferably used. For the purposes of the invention, water is not a suitable water miscible solvent.

The polyene fungicide is added to the alkaline or acidic aqueous liquid a polyene fungicide can be added to a final concentration of from 1000 to 50000 ppm. The polyene fungicide may be dissolved using well known methods. The polyene fungicide will be fully dissolved within a few minutes. The polyene fungicide can be added to the alkaline or acidic aqueous liquid before, at the same time or after the addition of the solvent. The polyene fungicide may be natamycin, nystatin, amphotericin B and lucencomycin. The preferred polyene fungicide is natamycin, which is also known under the brand names Delvocid®, Actistab® or Natamax®.

The stable ready-to-use aqueous composition of the polyene fungicide can be prepared by diluting the concentrated solution in a buffered aqueous liquid. The liquid is preferably water. The polyene fungicide is diluted to a final concentration of from 5 to 1000 ppm. The pH of said solution is preferably from 4 to 8 and more preferably from 5 to 7. The amount of solvent is preferably below 10% (w/w), more preferably below 5% (w/w) and most preferably below 2% (w/w). In general at least 0.1% (w/w) or preferably at least 0.2% (w/w) of the solvent is present in the ready-to-use composition of the invention. The pH is neutralized to pH from 4 to 8 by adding a pH neutralizing agent, for example an acid or alkaline compound, and/or preferably a buffer.

Any buffer known in the art can be used. Examples of suitable buffer systems are phosphate- and citrate buffers. The pH of the buffered system is preferably from 4 to 8 or more preferably from 5 to 7. According to another embodiment of the invention, the polyene fungicide is first dissolved under acid or alkaline conditions and thereafter is diluted by a mixture of water miscible solvents. In general a pH neutralising compound (an acid, alkaline compound or a buffer) is added.

The compositions of the invention contain a low amount of solvent and have pH values between 4 and 8. The solubility of the polyene fungicide natamycin in solvent/water systems is described in Brik, H.; "Natamycin" Analytical Profiles of Drug Substances 10, 513-561 (1981). The solubility of natamycin is 40 ppm in pure ethanol, while a solubility of 220 ppm can be achieved in an ethanol/water (4:1) system. The same has been reported when the solvent acetone is used. In an acetone/water (4:1) system, the maximum solubility of natamycin is 110 ppm. However solutions with high amounts of solvents were found to be less stable.

The solubility of the dissolved polyene fungicide can be further improved by the addition of solubilizers to a final concentration of from 0.1 to 5% w/w. Useful solubilizers may be surfactants of the anionic, cationic, non-ionic or amphoteric type. Examples of anionic surfactants are sodium lauryl sulfate and sodium dioctyl sulfo succinate. Examples of cationic surfactants are dodecyl ammonium chloride and hexadecyl triammonium bromide. Useful nonionic surfactants may be of the hydrophilic or of the hydrophobic type or a combination thereof. Examples of hydrophilic, nonionic surfactants are polyethyleneglycol-20 sorbitan monolaurate (also known as Tween 20), PEG-20 sorbitan monostearate (also known as Tween 60) and PEG-20 sorbitan monooleate (also known as Tween 80). Examples of hydrophobic, nonionic surfactants are sorbitan monolaurate (Span 20) and sorbitan monostearate (Span 60). Examples of amphoteric surfactants are alkyl betaines and alkylsulfobetaines. Also other known solubilizers such as lecithine or polyvinylpyrrolidone can be used.

The stability of the solubilized polyene fungicide can be further improved by adding a chelating agent to a final amount of from 10 to 10000 ppm, more preferably from 20 to 1000 ppm and most preferably from 30 to 300 ppm. Examples of chelating agents are ethylenediaminetetraacidic acid (EDTA) or its functional equivalents.

Also an anti-oxidation agent may be added to a final amount of from 10 to 10000 ppm. Examples of anti-oxidation agents are butylated hydroxyanisoles, riboflavine, ascorbic acid, citric acid and tocopherol.

The stable aqueous composition of polyene fungicide of the invention is preferably used for the treatment of various products for example food and feed products such as cheese, shredded cheese, meat products, sausages, cereals, animal feed, vegetables, fruits and ready-to-use meals. The stable composition can also easily be mixed with coating emulsions, such as the polyvinylacetate type, and applied to the abovementioned products, e.g. cheese. The stable solution can also be mixed with beverages such as juices, ice-tea, lemonades, wine and beer.

Agricultural applications such as the spraying of crops on the field or in greenhouses are also included in this invention. Examples of crops are vegetables, fruits, herbs, flowers and plants. Flower bulbs as such or the ones used for multiplication, seeds and seed-potatoes can also be treated with the composition of the invention. Also growth substrates can be treated with the composition of the invention. Examples of growth substrates are compost, earth, humus, casings or peat. The composition of the invention is especially useful for the treatment of growth substrates applied in greenhouses and for the cultivation of mushrooms. Furthermore, said compositions can be used in- and outside buildings, for example for the cleaning or prevention of fungal growth in building materials, production equipment, walls, wooden materials, such as cheese shelves, and packaging materials. These stable aqueous compositions of polyene fungicides can also be used for medical applications, such as the treatment of fungal infections of the skin or for the preparation of a medicament for the treatment of fungal infection for example the skin.

Fungal species which are less susceptible to natamycin are found among the genera *Penicillium, Verticillium* and *Aspergillus*. Such species with a higher tolerance may grow on natamycin treated products under certain conditions. An example of such a species is *Penicillium* discolor which may cause spoilage problems in the cheese industry. In less hygienic conditions and/or in the presence of high amounts of fungi in the environment, about 30-50 ppm of dissolved natamycin in an aqueous composition might be insufficient to prevent fungal growth. *P. discolor* can easily grow on cheese if the relative humidity in a cheese warehouse is kept at a too high level. This particular fungus may also develop shortly after production, when the moisture content of cheese is high. The composition of the invention can be added to the cheese coating or used to treat the cheese by a spraying or dipping treatment.

Most fermented sausages are produced at high temperatures and extremely high humidities. During and just after this fermentation process, fungal growth may easily occur. The composition of the invention will also be advantageous in such situations.

The composition of the invention, which comprises a higher amount of active dissolved natamycin may be used for treatment just before closing of the packaging of a product. After closing of the packaging, recontamination will normally not occur. A good example is shredded cheese. Spraying with a natamycin solution gives an enhanced antifungal activity, and the fungicide is also very well divided over the surface of the cheese particles. In addition, the composition can be applied without using stirring devices to stir the spraying solution, such as is necessary for natamycin suspensions. Further, a suspension may block the nozzles of the spraying devices, which does not happen when a solution is applied.

Due to an optimal availability, low natamycin concentrations of less than 10 ppm are extremely efficient at eliminating fungi present in beverages such as juices, ice tea, lemonades, wine and beer. At these low concentrations, all the natamycin will be dissolved. It is advantageous if the natamycin is added using a stock solution instead of a stock suspension. A solution offers many advantages: it is easy to mix with the end product, no stirring devices are required and the natamycin is instantly dissolved and therefore available. Of course these advantages are not limited to this specific example.

Cheese shelves are an example of a wooden material used in food industry Fungi may be present in the nerves of the wood and grow to the surface thereby contaminating the food products. A high antifungal activity for a short time is required to achieve an efficient cleaning.

Growth substrates for the cultivation of crops are often contaminated with phytopathogenic fungal species. Inactivation of these fungi requires an optimal antifungal activity in the short term. A good example is the treatment of the compost or top casing used in the mushroom industry. The compost contains fungi, which influence the development of the mushrooms during cultivation in a negative way. Examples of unwanted fungi are *Trichoderma* species and *Verticillium* species. These fungi should not develop during the cultivation of mushrooms or even better should not be present at all. Fungi clearly cause many problems in the mushroom industry. During cultivation growth conditions are optimal for both the mushrooms as well as the unwanted fungal species. Fungi are always present in the compost. Poor quality compost may contain a too high amount of fungi. These unwanted fungi can disturb the development of the mushroom mycelium through competition, which leads to lower yields.

Spraying of natamycin onto a surface, such as walls, equipment, cheese shelves or crops contaminated with fungi also requires an optimal amount of active natamycin. If a suspension is applied, the crystals will drip off from the material, such as the plant leaves or fruits, without having contributed to the antifungal activity.

Example 1

This example describes the rapid preparation of a stable aqueous composition of natamycin in a buffered aqueous system with enhanced solubility.

Preparation of the Natamycin Solutions (1)

An ethanolic aqueous solution having a pH of 12.8 was prepared by mixing 60 ml of a 0.04 N sodium hydroxide solution and 40 ml of 96% ethanol.

While stirring vigorously, 1 g of natamycin was added. The natamycin dissolved within 2 minutes.

Immediately after dissolution, the obtained concentrated natamycin solution was added to 20 l of a 0.01 M citrate buffer solution. A solution containing 57 ppm of natamycin and 0.2% of ethanol with a pH of 6.5 was obtained.

In a similar manner, a solution containing 101 ppm of natamycin and 0.4% of ethanol and a solution containing 202 ppm of natamycin and 0.8% of ethanol was obtained by adding the concentrated natamycin solution to 101 or 5 l of a 0.01 M citrate buffer respectively.

Preparation of the Natamycin Solutions (2)

Said solutions were also be prepared by dissolving 1 g of natamycin in water having a pH of 12.8. Immediately after dissolution, the concentrated natamycin solution was added to the buffer solution containing ethanol to provide the same final concentrations as described above.

Stability of the Solutions

The amount of natamycin in the compositions (1) was determined after 24 hours storage at 21° C. The amount of natamycin was determined using well-known methods (HPLC) and shown to be 57, 97 and 196 ppm respectively. Hardly any loss of activity was observed after 9 days storage at 6° C. The concentration of natamycin was 49, 100 and 170 ppm respectively. Even after storage for 9 days at 21° C., the concentration of natamycin of the composition containing 101 ppm at t=0 was 99 ppm.

Controls 1 g of natamycin was added to a neutral ethanolic aqueous system containing up to 40% of ethanol. Even after a few hours of stirring, it was not fully dissolved.

The natamycin did not dissolve when the same procedure as described above used without adding a solvent.

200 ppm of natamycin did not dissolve in a buffered aqueous system when the solvent was not present. Even when the solvent was present, 200 ppm of natamycin did not dissolve without first raising the pH to 12.8.

This Example clearly demonstrates that stable natamycin solutions can be prepared within a few minutes. The amount of dissolved natamycin of these solutions is at least 6 times higher than the maximum solubility in water at the same pH values.

Example 2

This Example describes the rapid preparation of a stable aqueous composition of natamycin in a non-buffered aqueous system with enhanced solubility.

A concentrated natamycin solution was prepared as described in Example 1 (1).

However, after diluting the concentrated natamycin solution in water, the pH was adjusted to 6.4-6.6 using HCL. Finally, solutions containing 101 and 202 ppm of natamycin were obtained.

The amount of natamycin in the compositions was determined after 24 hours storage at 21° C. The concentration of natamycin was 99 and 192 ppm respectively. Hardly any loss of activity was observed after 9 days storage at 6° C. The concentration of natamycin was 98 and 198 ppm respectively. Even after storage for 9 days at 21° C. the concentration of natamycin in the composition containing 101 ppm at t=0 was 82 ppm.

This Example also clearly demonstrates that stable natamycin solutions can be prepared within a few minutes. The amount of dissolved natamycin of these solutions is at least 6 times higher than the maximum solubility in water at the same pH values

The invention claimed is:

1. A method for the production of a stable aqueous natamycin composition, the method comprising the steps of:
   a) mixing natamycin, water and a water-miscible alcoholic solvent and adjusting the pH to prepare a concentrated aqueous natamycin solution having a pH of from 10 to 14;
   b) diluting the concentrated solution prepared in step (a) with an aqueous solution to produce the stable aqueous natamycin composition, said composition comprising at least 0.1% (w/w) but below 10% (w/w) of the water-miscible alcoholic solvent and having a pH of between 4 and 8 wherein natamycin is present in the stable aqueous natamycin composition in a concentration of from 5 to 50 ppm.

2. A method according to claim 1, wherein the aqueous solution used for dilution contains a pH neutralizing agent, a buffer or both.

3. A method according to claim 1, wherein natamycin is present in the concentrated aqueous solution in a concentration of from 1000 to 50,000 ppm.

4. A method according to claim 1, wherein the water-miscible alcoholic solvent.

5. A method according to claim 1, wherein the ratio of water-miscible alcoholic solvent to water in the concentrated solution is from 30:70 to 70:30.

6. A method according to claim 1, wherein the natamycin in step (a) is completely dissolved.

7. A method according to claim 1, wherein in step (a) first an aqueous composition comprising a water-miscible alcoholic solvent is prepared and then natamycin is added to the composition.

8. A method according to claim 1 further comprising the step of adding a solubilizer.

9. A method according to claim 8, wherein the final concentration of the solubilizer is from 0.1 to 5% (w/w).

10. A method according to claim 1 further comprising the step of adding a chelating agent.

11. A method according to claim 10, wherein the final concentration of the chelating agent is from 10 to 10,000 ppm.

12. A method according to claim 1 further comprising the step of adding an anti-oxidation agent.

13. A method according to claim 12, wherein the final concentration of the anti-oxidation agent is from 10 to 10,000 ppm.

14. A method for treating a product with a stable aqueous natamycin composition, the method comprising the steps of:
   a) producing a stable aqueous natamycin composition according to the method of claim 1;
   b) treating a product with the stable aqueous natamycin composition.

15. A method according to claim 14, wherein the product is selected from the group consisting of food products, feed products, agricultural products, building materials, production equipment, walls, wooden materials and packaging materials.

16. A method according to claim 15, wherein the agricultural products are selected from the group consisting of vegetables, fruits, herbs, flowers, flower bulbs, seeds, seed-potatoes, growth substrates and plants.

* * * * *